United States Patent
Chen et al.

(10) Patent No.: US 10,231,706 B2
(45) Date of Patent: Mar. 19, 2019

(54) INTEGRATED MULTIMODALITY INTRAVASCULAR IMAGING SYSTEM THAT COMBINES OPTICAL COHERENCE TOMOGRAPHY, ULTRASOUND IMAGING, AND ACOUSTIC RADIATION FORCE OPTICAL COHERENCE ELASTOGRAPHY

(71) Applicant: The Regents of the University of California, Oakland, CA (US)

(72) Inventors: Zhongping Chen, Irvine, CA (US); Wenjuan Qi, Irvine, CA (US); Rui Li, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 378 days.

(21) Appl. No.: 14/213,904

(22) Filed: Mar. 14, 2014

(65) Prior Publication Data
US 2015/0351722 A1     Dec. 10, 2015

Related U.S. Application Data

(60) Provisional application No. 61/783,178, filed on Mar. 14, 2013.

(51) Int. Cl.
*A61B 8/00*     (2006.01)
*A61B 8/08*     (2006.01)
(Continued)

(52) U.S. Cl.
CPC ............ *A61B 8/485* (2013.01); *A61B 5/0035* (2013.01); *A61B 5/0066* (2013.01);
(Continued)

(58) Field of Classification Search
CPC ... A61B 6/5229; A61B 6/4417; A61B 5/0059; A61B 5/0066; A61B 8/12; A61B 8/445; A61B 8/4281; A61B 8/485
(Continued)

(56) References Cited

U.S. PATENT DOCUMENTS

| | | | |
|---|---|---|---|
| 2009/0043191 A1* | 2/2009 | Castella | A61B 5/0066 600/425 |
| 2009/0203991 A1* | 8/2009 | Papaioannou | A61B 5/0066 600/421 |

(Continued)

OTHER PUBLICATIONS

Wang, Ruikang K., Sean Kirkpatrick, and Monica Hinds. "Phase-sensitive optical coherence elastography for mapping tissue microstrains in real time." Applied Physics Letters 90.16 (2007): 164105.*
(Continued)

*Primary Examiner* — Carolyn Pehlke
(74) *Attorney, Agent, or Firm* — Nguyen & Tarbet Law Firm

(57) ABSTRACT

An integrated intraluminal imaging system includes an optical coherence tomography interferometer (OCT), an ultrasound subsystem (US) and a phase resolved acoustic radiation force optical coherence elastography subsystem (PR-RAF-OCE). The steps include performing OCT to generate a returned optical signal, performing US imaging to generate a returned ultrasound signal, performing PRARF-OCE to generate a returned PR-ARF-OCE signal by generating a amplitude modulated ultrasound beam or chirped amplitude modulated ultrasound beam to frequency sweep the acoustic radiation force, measuring the ARF induced tissue displacement using phase resolved OCT, and the frequency dependence of the PR-ARF-OCE signal, processing the returned optical signal, the returned ultrasound signal and the measured frequency dependence of the returned PR-ARF-OCE optical coherence elastographic signal to quantitatively measure the mechanical properties of the identified tissues with both spectral and spatial resolution using enhanced materials response at mechanically resonant frequencies.

2 Claims, 11 Drawing Sheets
(11 of 11 Drawing Sheet(s) Filed in Color)

(51) Int. Cl.
    *A61B 5/00*     (2006.01)
    *A61B 5/02*     (2006.01)
    *A61B 8/12*     (2006.01)
(52) U.S. Cl.
    CPC ............ *A61B 5/02007* (2013.01); *A61B 8/12* (2013.01); *A61B 8/445* (2013.01); *A61B 8/4416* (2013.01); *A61B 8/5261* (2013.01)
(58) Field of Classification Search
    USPC .............................. 600/427, 466, 467, 478
    See application file for complete search history.

(56)             References Cited

U.S. PATENT DOCUMENTS

2014/0187904 A1*  7/2014  Razani ................. A61B 5/0066
                                                    600/407
2015/0209564 A1*  7/2015  Lewin .................... A61N 7/00
                                                    601/2

OTHER PUBLICATIONS

Wang, Ruikang K., and Alfred L. Nuttall. "Phase-sensitive optical coherence tomography imaging of the tissue motion within the organ of Corti at a subnanometer scale: a preliminary study." Journal of biomedical optics 15.5 (2010): 056005-056005.*

Adie, Steven G., et al. "Spectroscopic optical coherence elastography." Optics express 18.25 (2010): 25519-25534.*

Kennedy, Brendan F., et al. "In vivo three-dimensional optical coherence elastography." Optics Express 19.7 (2011): 6623-6634.*

Qi, Wenjuan, et al. "Phase-resolved acoustic radiation force optical coherence elastography." Journal of biomedical optics 17.11 (2012): 110505-110505.*

Liang, Xing, et al. "Dynamic spectral-domain optical coherence elastography for tissue characterization." Optics express 18.13 (2010): 14183-14190.*

Sun, Cuiru, Beau Standish, and Victor XD Yang. "Optical coherence elastography: current status and future applications." Journal of biomedical optics 16.4 (2011): 043001-043001.*

Urban, Matthew W., Mostafa Fatemi, and James F. Greenleaf. "Modulation of ultrasound to produce multifrequency radiation forces." the Journal of the Acoustical Society of America 127.3 (2010): 1228-1238.*

Yin, Jiechen, et al. "Novel combined miniature optical coherence tomography ultrasound probe for in vivo intravascular imaging." Journal of biomedical optics 16.6 (2011): 060505-060505.*

Li, Chunhui, et al. "Evaluating elastic properties of heterogeneous soft tissue by surface acoustic waves detected by phase-sensitive optical coherence tomography." Journal of biomedical optics 17.5 (2012): 0570021-05700210.*

Liang, Xing, Vasilica Crecea, and Stephen A. Boppart. "Dynamic optical coherence elastography: a review." Journal of innovative optical health sciences 3.04 (2010): 221-233.*

Emelianov, Stanislav Y., et al. "Combined ultrasound, optoacoustic, and elasticity imaging." Biomedical Optics 2004. International Society for Optics and Photonics, 2004.*

* cited by examiner

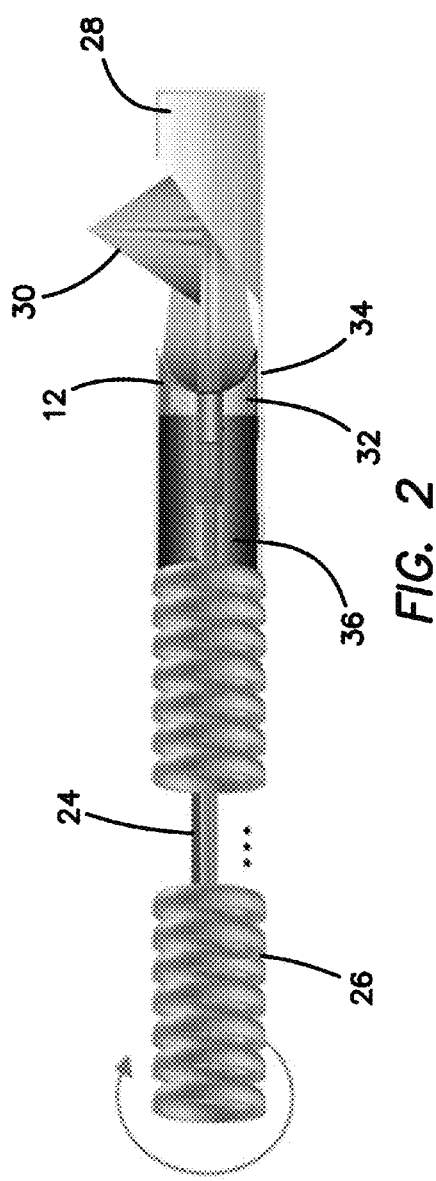
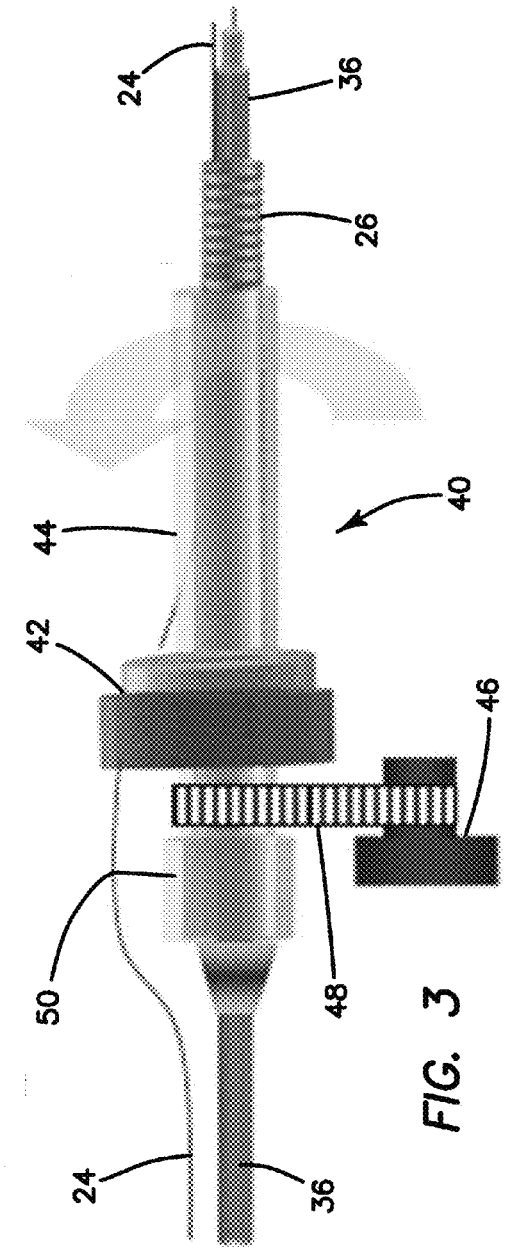
FIG. 2
FIG. 3

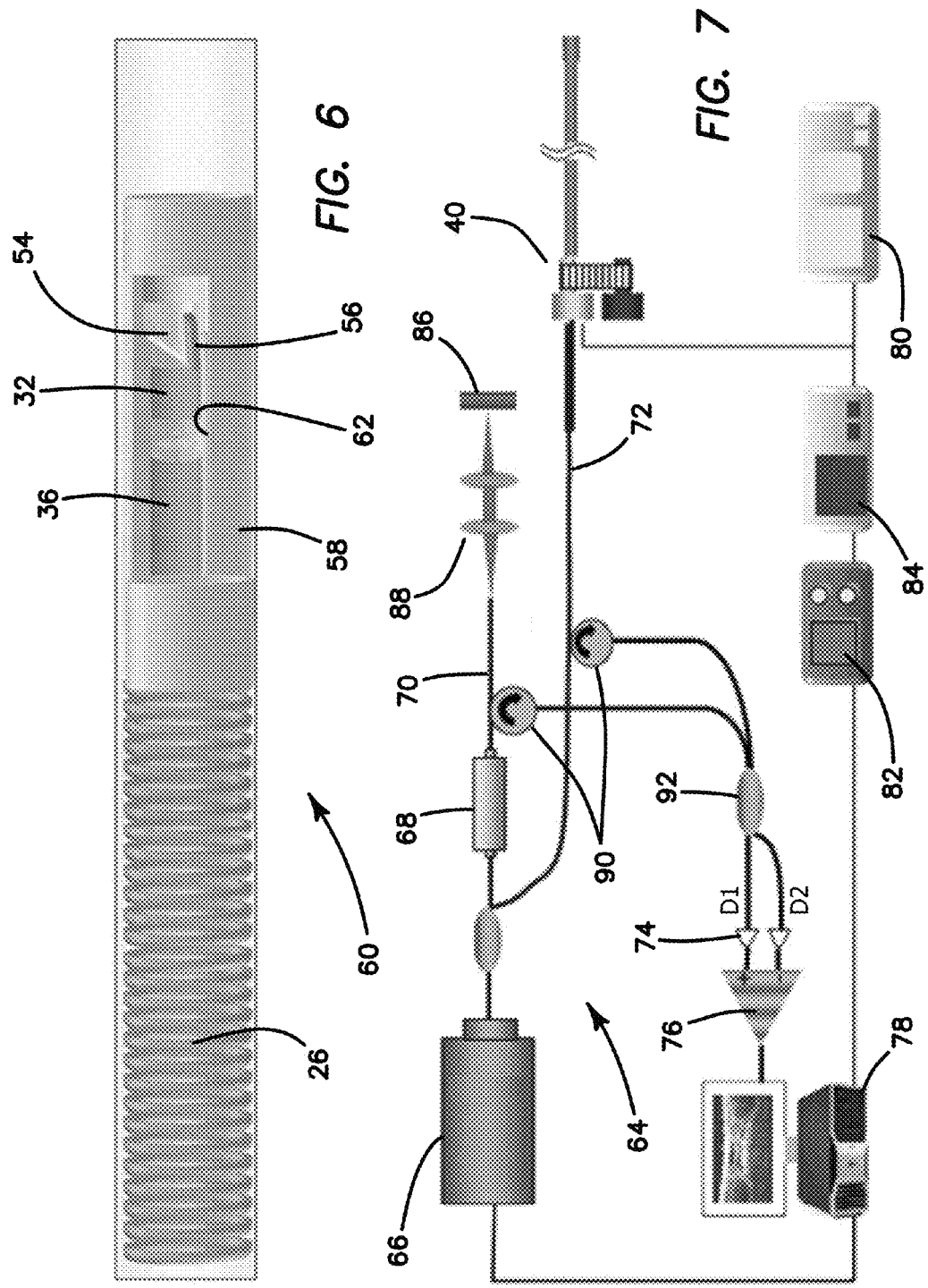

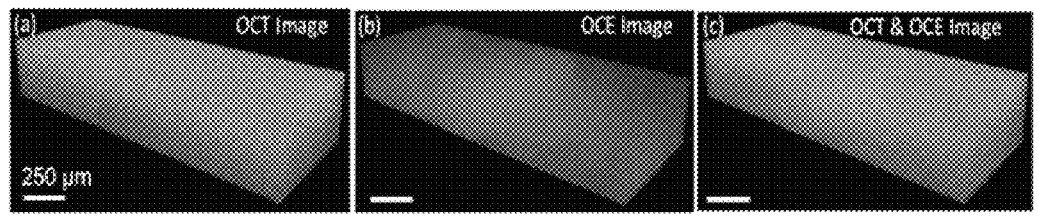
FIG. 15A     FIG. 15B     FIG. 15C
FIG. 16A
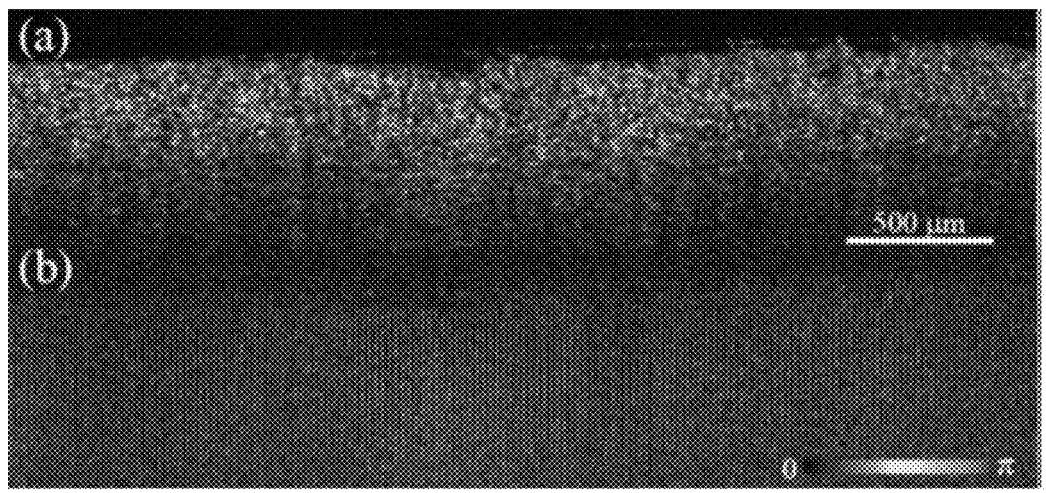
FIG. 16B

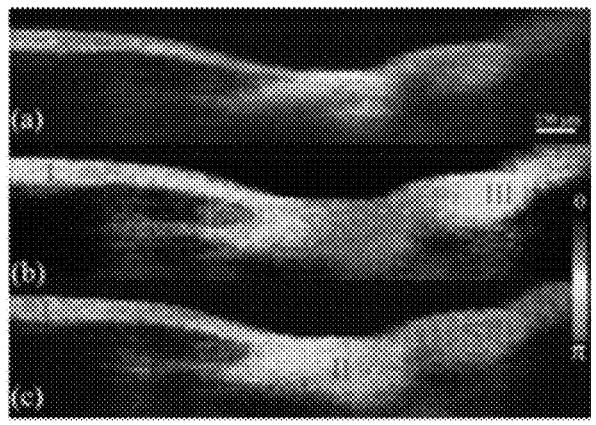
FIG. 17A
FIG. 17B
FIG. 17C
FIG. 17D
FIG. 17E
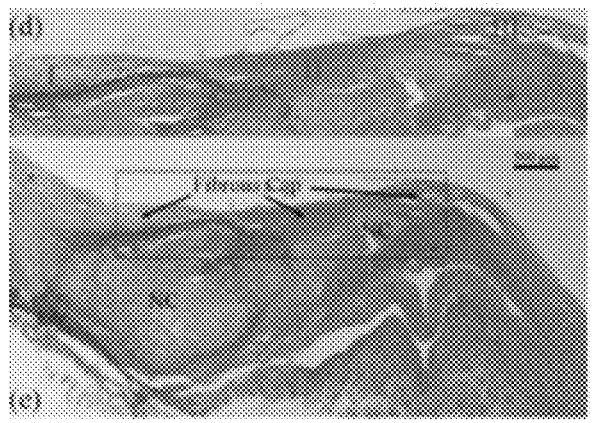

INTEGRATED MULTIMODALITY INTRAVASCULAR IMAGING SYSTEM THAT COMBINES OPTICAL COHERENCE TOMOGRAPHY, ULTRASOUND IMAGING, AND ACOUSTIC RADIATION FORCE OPTICAL COHERENCE ELASTOGRAPHY

RELATED APPLICATIONS

The present application is related to U.S. Provisional Patent Application, Ser. No. 61/783,178, filed on Mar. 14, 2013, which is incorporated herein by reference and to which priority is claimed pursuant to 35 USC 119.

GOVERNMENT RIGHTS

This invention was made with government support under contract numbers R01EB-10090, R01EY-021519, R01HL-105215, R01HL-103764, and P41EB-015890 awarded by the National Institutes of Health, and Air Force Office of Scientific Research (FA9550-04-0101). The government has certain rights in the invention.

BACKGROUND

Field of the Technology

The disclosure relates to the field of medical device, multimodality intravascular imaging systems, multimodality endoscopic imaging systems, optical coherence elastography, and acoustic radiation force systems.

Description of the Prior Art

Atherosclerosis is a complex disease in which multiple plaques build up within the arteries. The major cause of cardiovascular death in heart attacks (86%) and from brain aneurysm (45%) are due to less obtrusive plaques known as "vulnerable plaques" that rupture suddenly and trigger a blood clot or thrombus that blocks blood flow. Early detection of plaque lesions is the first and necessary step in preventing the lethal consequences of atherosclerosis. Diagnosis of the latent vulnerability of a plaque lesion relies on both tissue structural and biomechanical properties. The thickness of the fibrous cap, the thickness of the full plaques, and the vascular tissue biomechanical properties are all parameters that correlate with the vulnerability of the lesion. Although currently no clinical trials have confirmed the successful treatment of vulnerable plaque and reduction in cardiovascular mortality and morbidity, advances in clinical management of atherosclerosis require refinements to current therapies or new strategies with strict monitoring of all aspects of this epidemic disease.

Cancer is a leading worldwide cause of death. Early diagnosis of cancer increases the survival rate and reduces treatment. A cancerous tumor is normally stiffer than the background of normal soft tissue. For example, prostate cancer is the second most common cancer among American men, and is, behind lung cancer, the second most common cause of cancer deaths among men. Current diagnostic techniques, including digital rectal exam (DRE) and the measurement of blood prostate-specific antigen (PSA) levels, are insufficient for guiding treatment. Tissue biopsies are needed for diagnosis. The chief prostate cancer imaging technique is ultrasound, but grayscale ultrasound imaging is only 50-60% accurate and transrectal ultrasound (TRUS) is even less accurate. Ultrasound also has difficulty differentiating cancer from other diseases, such as benign prostatic hyperplasia (BPH) and prostatitis. Despite advances in ultrasound techniques such as color and power Doppler, and the introduction of ultrasound contrast agents, TRUS is still limited in accuracy and therefore only used to guide biopsy.

Currently, many biomedical imaging techniques aimed at imaging and assessing vulnerable plaques have been reported in the literature, including angiography, magnetic resonance imaging (MRI), intravascular ultrasound (IVUS), optical coherence tomography (OCT), intravascular near infrared spectral imaging, intravascular fluorescence imaging, and intravascular photoacoustic tomography (IVPAT).

Angioscopy allows the plaque to be visualized with high sensitivity, but the morphologic characterization of the plaque is unreliable because of the lack of estimation of cap thickness or lipid content. Even though MRI is used to study the progression and regression of plaque over time, its insufficient resolution cannot render accurate measurements.

IVUS has limited resolution and sensitivity to assess the thickness of the thin fibrous cap and for plaque classifications. OCT has a limited imaging depth and cannot quantify the full thickness of the plaque. Recently, Sawada et al. studied the feasibility of the combined use of IVUS and OCT data (images acquired separately) for detecting thin-cap fibroatheroma (TCFA) from 56 patients. The results clearly show that neither modality alone is sufficient for detecting TCFA.

The limitation of NIRS, Raman and fluorescence imaging is that they lack the capability of tomographic imaging. IVUS lacks the required high resolution to quantify the thickness of the fibrous cap. We recently reported the integrated OCT/US system for intravascular imaging. However, this system lacks the capability to resolve tissue composition in plaque lesions. Although each optical probing technique provides access to relevant diagnostic parameters, integration of several modalities is necessary to gather the information required to establish a robust method for early detection of plaque.

Elastography is an imaging technique, which measures the local deformation of tissue induced by stresses to estimate the strain and stiffness which are directly related to the biomechanical properties. The mechanical properties of tissue give important diagnostic information about many vascular diseases such as hypertension and coronary atherosclerosis. Due to the small dimensions involved, time varying blood flow, and presence of multiple plaques of different sizes, geometries, and compositions, arterial elastography is more challenging than other elastographies such as breast tissue elastography. Recently several elastography techniques have utilized other biomedical imaging modalities such as ultrasound, MRI, and OCT to detect the plaques in coronary arteries. For all elastography techniques, the resolution is determined by the underlying imaging modality.

Optical coherence elastography (OCE) has a superior micrometer scale resolution and is therefore suitable for imaging subtle mechanical changes in the early stages of disease. Excitation and detection are generally two characteristics or components of an OCE system. There are two main categories of OCE with respect to the excitation method: static/quasi-static excitation OCE and dynamic excitation OCE. The former applies compression to the subject statically/quasi-statically and measures the relaxation dynamics, which has limited imaging speed for in vivo imaging. The latter dynamically excites the subject using various waveforms and detects the induced displacement in a gated time window, which enables a much higher imaging speed and makes it possible for in vivo imaging. For the detection system, a phase-resolved OCT system can detect displacement with nanometer sensitivity, which is especially important for intravascular imaging as better sensitivity in displacement measurement means minimal force is needed to be applied to a vessel wall to quantify tissue mechanical properties. Phase-resolved dynamic OCE had been investigated previously for shear wave propagation detection, but this method requires separation between excitation and detection points, which limits the speed and spatial resolution. Adaptation of this method for in vivo real time 2D and 3D vascular elastography is not viable.

BRIEF SUMMARY

The illustrated embodiments are directed to diagnosis and management of various cancers, vascular diseases, and other diseases that exhibit changes in biomechanical properties of tissue.

One goal of the illustrated embodiments of the invention is the development of an integrated intravascular imaging system that combines optical coherence tomography, ultrasound, phase resolved acoustic radiation force optical coherence elastography (OCT/US/PR-ARF-OCE) for identifying the different types of plaques, such as lipid inclusion, fibrous plaque and calcified plaque, and to measure structure and mechanical properties of tissue simultaneously The illustrated embodiments of the invention include a multimodal intravascular/endoscopic imaging system that combines intravascular optical coherence tomography (OCT), ultrasound (US), and the phase-resolved acoustic radiation force optical coherence elastography (PR-ARF-OCE).

The multimodal intravascular imaging system is unique in that it combines the advantages of high spatial resolution of OCT, broad imaging depth of US, and biomechanical/molecular contrast of PR-ARF-OCE.

This multi-modal imaging strategy in a single system permits the use of a single disposable guide wire and catheter, thereby reducing costs to hospitals and patients, and improving prognosis by early detection.

The ARF-OCE combines the high-speed excitation of ARF with sub-micrometer/nanometer detection sensitivity of phase resolved OCT. This elastography technique allows high-speed and high-resolution point-by-point mapping of local strains in atherosclerotic coronary tissue, which provide critical information to assess the vulnerability of plaques.

This is especially important for intravascular imaging, as better sensitivity in displacement measurement means minimal acoustic radiation forces are need be applied to a vessel wall to quantify tissue mechanical properties.

A spectral and resonant PR-ARF-OCE technique, where a chirped ultrasound signal is used to generate a frequency sweep of ARF to measure the frequency dependence of OCE signal, can be used to measure quantitatively the mechanical properties of tissue and different tissues with both spectral and spatial resolution. This method takes advantage of the fact that materials response is enhanced at their mechanical resonant frequencies, which can be used effectively distinguish samples with varying stiffness.

In addition to cardiovascular diseases, this technique can also be applied to other vascular diseases such as peripheral vascular diseases, and brain aneurysms. The technique can be applied to any diseases where knowing the structure and biomechanical properties of tissue or organ are important, such as cancers.

Thus, it can be appreciated that the illustrated embodiments of the invention are directed to an integrated intraluminal imaging system for diagnosis and management of a disease exhibiting changes in biomechanical properties of tissues. The integrated intraluminal imaging system includes an intraluminal probe, and an optical coherence tomography interferometer including an optical fiber disposed in the intraluminal probe. The optical fiber delivers an optical beam and receives a returned optical signal through the intraluminal probe from the tissues. An ultrasound subsystem having an ultrasound transducer is disposed in the intraluminal probe. The transducer delivers an ultrasound beam and receives a returned ultrasound signal through the intraluminal probe from the tissues. An acoustic generator is coupled to the ultrasound transducer for delivering an acoustic radiation force (ARF) to the tissues. The optical coherence tomography interferometer receives a returned ARF optical signal due to displacement of the tissues in response to the acoustic radiation force from which returned ARF optical signal, a phase resolved acoustic radiation force optical coherence elastography image can be formed. A computer is coupled to optical coherence tomography interferometer, to the ultrasound transducer, and to the acoustic generator for controlling the same and for processing the returned optical signal, the returned ultrasound signal and the returned ARF optical signal to form an image to identify tissues with different biomechanical properties and to measure structural and mechanical properties of the identified tissues simultaneously.

The computer combines intravascular optical coherence tomography (OCT), ultrasound (US), and the phase-resolved acoustic radiation force optical coherence elastography (PR-ARF-OCE) to generate high spatial resolution OCT images with broad imaging depth of US, and biomechanical/molecular imaging contrast of PR-ARF-OCE.

The integrated intraluminal imaging system further includes a single disposable catheter into which the intraluminal probe is disposed, whereby costs are reduced and hence prognosis improved by early detection.

The acoustic generator provides acoustic radiation force with high-speed excitation of the tissues and the optical coherence tomography interferometer detects displacement of the tissues in response to the high-speed excitation with a sub-micrometer/nanometer sensitivity of phase resolved OCT.

The computer processes the returned ARF optical signal to provide high-speed and high-resolution point-by-point mapping of local strains in tissues, which processing provides critical information to assess the vulnerability of coronary plaques for intravascular imaging, and so that the acoustic generator is adjustable to deliver low intensity acoustic radiation forces to the coronary plaques to quantify tissues mechanical properties.

The ultrasound subsystem generates a chirped amplitude modulated ultrasound beam used to generate a frequency sweep of the acoustic radiation force delivered by the ultrasound transducer to measure frequency dependence of the returned ARF optical signal, where the computer processes the measured frequency dependence of the returned ARF optical signal to quantitatively measure the mechanical properties of the identified tissues with both spectral and spatial resolution using enhanced materials response at mechanically resonant frequencies to distinguish tissues with varying stiffness.

The computer processes the measured frequency dependence of the returned ARF optical signal to identify tissues with cardiovascular disease, peripheral vascular disease, brain aneurysm, cancer, hypertension, coronary atherosclerosis or a disease identifiable by the structural and biomechanical properties of the diseased tissues.

The illustrated embodiments also include a method of using an integrated intraluminal imaging system for diagnosis and management of a disease exhibiting changes in biomechanical properties of tissues. The method comprises the steps of providing an intraluminal probe, providing an optical coherence tomography interferometer including an optical fiber disposed in the intraluminal probe, delivering an optical beam through the intraluminal probe to the tissues, receiving a returned optical signal through the intraluminal probe from the tissues for communication thereof to the optical coherence tomography interferometer, providing an ultrasound subsystem having an ultrasound transducer disposed in the intraluminal probe, delivering an ultrasound beam from the transducer, receiving a returned ultrasound signal through the intraluminal probe from the tissues in an ultrasound receiver, providing an acoustic generator generating an acoustic radiation force (ARF) signal coupled to the ultrasound transducer, delivering an acoustic radiation force (ARF) to the tissues from the ultrasound transducer through the intraluminal probe, receiving a returned ARF optical signal in the optical coherence tomography interferometer measuring displacement of the tissues in response to the acoustic radiation force, and processing the returned optical signal, the returned ultrasound signal and the returned ARF optical signal in a computer to form an image to identify tissues with different biomechanical properties and to measure structural and mechanical properties of the identified tissues simultaneously.

The step of processing the returned optical signal, the returned ultrasound signal and the returned ARF optical signal in a computer to form an image combines image data from intravascular optical coherence tomography (OCT), ultrasound (US), and the phase-resolved acoustic radiation force optical coherence elastography (PR-ARF-OCE) to generate high spatial resolution OCT images with broad imaging depth of US, and biomechanical/molecular imaging contrast of PR-ARF-OCE.

The method further includes the step of providing a single disposable catheter into which the intraluminal probe is disposed, whereby costs are reduced and hence prognosis improved by early detection.

The step of delivering an acoustic radiation force (ARF) to the tissues delivers acoustic radiation force with high-speed excitation of the tissues and where receiving a returned ARF optical signal in the optical coherence tomography interferometer detects displacement of the tissues in response to the high-speed excitation with a sub-micrometer/nanometer sensitivity of phase resolved OCT.

The step of processing the returned optical signal, the returned ultrasound signal and the returned ARF optical signal in the computer comprises forming an image from the returned ARF optical signal to provide high-speed and high-resolution point-by-point mapping of local strains in tissues to provide information to assess a vulnerability of coronary plaques for intravascular imaging, and where delivering an acoustic radiation force (ARF) to the tissues from the ultrasound transducer is delivered with a safe acoustic radiation force to the coronary plaques to quantify tissues mechanical properties.

The step of providing an acoustic generator generating an acoustic radiation force (ARF) signal coupled to the ultrasound transducer comprises generating a chirped amplitude modulated ultrasound beam to frequency sweep the acoustic radiation force delivered by the ultrasound transducer, where processing the returned optical signal, the returned ultrasound signal and the returned ARF optical signal comprising measuring frequency dependence of the returned ARF optical signal, and further comprising processing the measured frequency dependence of the returned ARF optical signal to quantitatively measure the mechanical properties of the identified tissues with both spectral and spatial resolution using enhanced materials response at mechanically resonant frequencies to distinguish tissues with varying stiffness.

The step of processing the measured frequency dependence of the returned ARF optical signal comprises identifying tissues with cardiovascular disease, peripheral vascular disease, brain aneurysm, cancer, hypertension, coronary atherosclerosis or a disease identifiable by the structural and biomechanical properties of the diseased tissues.

The step of processing the returned optical signal, the returned ultrasound signal and the returned ARF optical signal comprises performing optical coherence elastography (OCE) with micrometer scale resolution for imaging mechanical changes in the early stages of disease, where performing optical coherence elastography (OCE) includes static/quasi-static excitation OCE and dynamic excitation OCE, where static/quasi-static excitation OCE includes compressing the tissues and measuring relaxation dynamics, and where dynamic excitation OCE includes dynamically exciting the tissues using various waveforms and detecting the induced displacement in a gated time window, where receiving a returned optical signal through the intraluminal probe from the tissues for communication thereof to the optical coherence tomography interferometer uses a phase-resolved optical coherence tomography interferometer to detect displacement with nanometer and submicron sensitivity using minimal acoustic radiation force applied to a vessel wall to quantify mechanical properties of the tissues.

The step of delivering an acoustic radiation force (ARF) to the tissues from the ultrasound transducer through the intraluminal probe comprises applying pressure to the tissues, and where receiving a returned ARF optical signal in the optical coherence tomography interferometer measuring displacement of the tissues in response to the acoustic radiation force comprises using phase-resolved OCT to evaluate the elastic properties of vascular tissues to combine high-speed excitation by acoustic radiation forces with sub-micrometer/nanometer detection sensitivity of phase resolved OCT to achieve high-speed and high-resolution point-by-point mapping of local strains in atherosclerotic coronary tissues to assess the vulnerability of plaques.

The step of delivering an acoustic radiation force (ARF) to the tissues from the ultrasound transducer through the intraluminal probe comprises using a known excitation signal to sweep different frequencies and measuring the frequency response of the tissues to detect differences between normal and diseased tissues with altered elasticity by sensing resonance frequencies between tissues.

The step of using a known excitation signal to sweep different frequencies and measuring the frequency response of the tissues comprises differentiating between various plaque components, based on different mechanical properties of fibrous and fatty plaques.

The step of processing the returned optical signal, the returned ultrasound signal and the returned ARF optical signal in a computer to form an image comprises imaging and diagnosing different types of vulnerable plaques and monitoring therapeutic efficacy at an earlier stage.

A tangible memory medium having an image stored therein, which image is generated by the above methods. The tangible memory medium includes a computer memory element or a hardcopy printout of the image generated by the computer.

The embodiments of the invention also include a method of using an integrated intraluminal imaging system including an optical coherence tomography interferometer (OCT), an ultrasound subsystem (US) and a phase resolved, acoustic radiation force optical coherence elastography subsystem (PR-RAF-OCE). The method includes the steps of performing optical coherence tomography to generate a returned optical signal, performing ultrasound imaging to generate a returned ultrasound signal, performing phase resolved acoustic radiation force optical coherence elastography to generate a returned ARF optical coherence elastographic signal by generating a chirped ultrasound beam to frequency sweep the acoustic radiation force, measuring frequency dependence of the returned ARF optical signal, processing the returned optical signal, the returned ultrasound signal and the measured frequency dependence of the returned ARF optical coherence elastographic signal to quantitatively measure the mechanical properties of the identified tissues with both spectral and spatial resolution using enhanced materials response at mechanically resonant frequencies to distinguish tissues with varying stiffness, to identify tissues with different biomechanical properties and to measure structural and mechanical properties of the identified tissues simultaneously. The ARF optical signal is the OCT signal while ARF is applied to the tissue. Phase resolved OCT is used to process the OCT signal to determine ARF induced displacement. Thus, it should be understood that there are two main separate return signals OCT and US. The ARF optical signal is the returned OCT signal measuring the effect of acoustic radiation force (ARF) on the tissue.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is a longitudinal cutaway diagram of one embodiment of the probe of the invention.

FIG. 3 is a diagrammatic side view of a double clad fiber (DCF) rotary joint used in the catheter including the intraluminal probe of FIG. 2.

FIG. 6 is a longitudinal cutaway diagram of still another embodiment of the probe of the invention where the ultrasound transducer is distally located in the intraluminal probe adjacent a prism.

FIG. 7 is a schematic diagram of one embodiment of the integrated intraluminal imaging system of the invention.

FIG. 12a is an OCT image. FIG. 12b is a PR-ARF-OCE image.

FIG. 15a is an OCT structural image of a phantom. FIG. 15b is a resonant ARF-OCE image of the phantom. FIG. 15c is a fused image of the agar phantom with a piece of silicone embedded inside, stimulated at a fixed frequency of 1250 Hz. The silicone shows distinctive vibration amplitude due to its resonance. The agar phantom, however, vibrates much less since the driving frequency is far away from its resonant frequency.

FIG. 16a is an OCT image and FIG. 16b is an OCE image for a homogeneous phantom. The ARF-induced displacement is confirmed to be uniform within the area scanned.

FIGS. 17a-17c illustrated the frequency response of a human coronary artery. FIG. 17a is an OCT morphological image of the coronary artery segment in the dotted area in the microphotograph of FIG. 17e. FIGS. 17b and 17c are resonant-ARF-OCE images showing frequency response at 500 Hz and 800 Hz respectively. A higher vibration amplitude is measured on the left and right side of the resonant-ARF-OCE image in FIG. 17b at 500 Hz, corresponding to the thin loose fibrous cap. High vibration is detected at 800 Hz at the center of the NCFA at FIG. 17c corresponding to a thicker and denser portion of the fibrous cap. FIGS. 17c and 17d are histological sections showing a necrotic core fibroatheroma with a fibrous cap (arrows) overlying a large necrotic core. FIG. 17e is a close-up view of the scanned area of plaque in the dotted area in FIG. 17e.

Figure 1A:
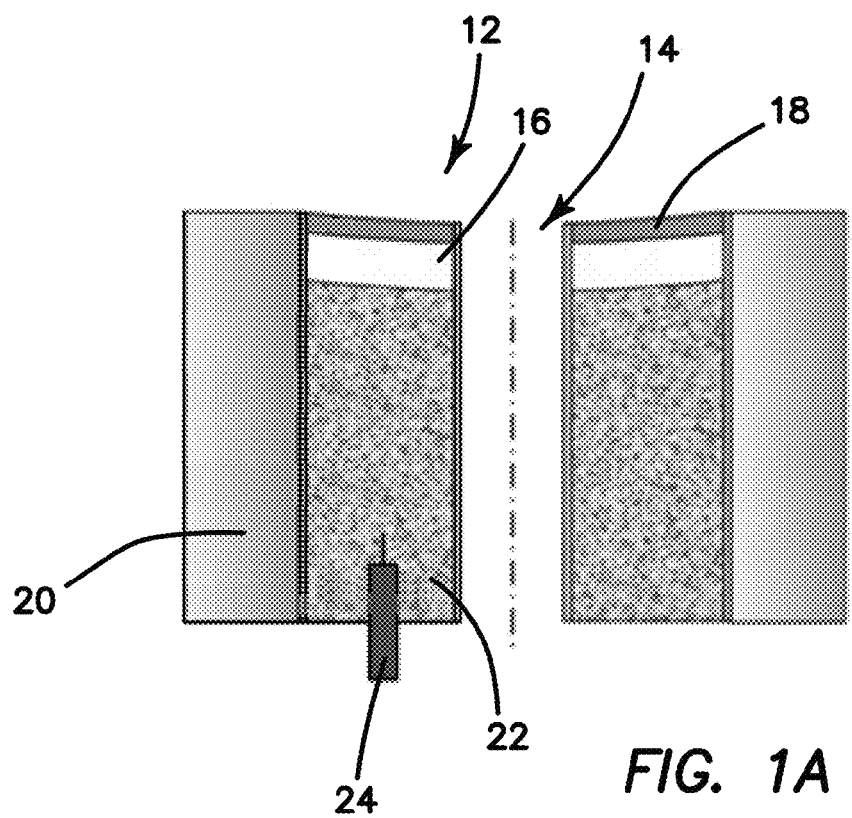
FIGS. 1a and 1b are side cutaway and top plan views respectively of an ultrasound transducer used in the intraluminal probe of the invention.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

We have developed a PR-ARF-OCE system 10 that uses an acoustic wave generated acoustic radiation force to apply pressure to the tissue and uses phase-resolved OCT to evaluate the elastic properties of vascular tissue. The ARF-OCE combines the high-speed excitation of ARF with sub-micrometer/nanometer detection sensitivity of phase resolved OCT. This elastography technique allows high-speed and high-resolution point-by-point mapping of local strains in atherosclerotic coronary tissue, which provide critical information to assess the vulnerability of plaques. Using a known excitation signal also allows us to sweep different frequencies and measuring the frequency response of tissues in order to detect the differences between normal and diseased tissue with altered elasticity by sensing resonance frequencies between tissues. Since the mechanical properties of fibrous and fatty plaques are different, PR-ARF-OCE also has the potential to differentiate between various plaque components.

The integrated OCT/US/PR-ARF-OCE provides the physician with a powerful tool for imaging and diagnosing vulnerable plaques and monitoring therapeutic efficacy at an earlier stage. Although one can perform OCT, US, PR-ARF-OCE separately, the cost of separate disposable guide wires and catheters for OCT, US, and PR-ARF-OCE are recurring costs and is unnecessary high due largely to individual sterilization. Therefore, it is significantly advantageous to integrate these three technologies into a single system to exploit the various features of these high-resolution technologies. If all three modalities are used to simultaneously acquire vascular images through the same disposable guide wire and catheter, then the cost of imaging to hospitals and radiology suites can be reduced considerably.

A PR-ARF-OCE system that uses an acoustic wave generated ARF to apply pressure to the tissue and uses phase-resolved OCT to evaluate the elastic properties of vascular tissue. The ARF-OCE combines the high-speed excitation of ARF with sub-micrometer/nanometer detection sensitivity of phase resolved OCT. This elastography technique allows high-speed and high-resolution point-by-point mapping of local strains in atherosclerotic coronary tissue, which provide critical information to assess the vulnerability of plaques. Using a known excitation signal also allows us to sweep different frequencies and measuring the frequency response of tissues in order to detect the differences between normal and diseased tissue with altered elasticity by sensing resonance frequencies between tissues. Since the mechanical properties of fibrous and fatty plaques are different, PR-ARF-OCE also has the potential to differentiate between various plaque components.

The disclosed multimodal intravascular imaging system 10 is unique in that it combines the advantages of high spatial resolution of OCT, broad imaging depth of US, and biomechanical/molecular contrast of PR-ARF-OCE. Visualizing plaques to help understand the progression of disease and to aid in diagnosis and treatment is highly desirable. Both in vitro and in vivo studies have shown that fatty tissue has higher strain than fibrous plaques and the presence of vulnerable plaques is the high strain areas surrounded by low strain areas. More recent studies have pointed to the vulnerability and rupturing of the plaques being related to the stress on the fibrous cap, the cap thickness, arterial remodeling, and the composition of the plaques. Therefore it is important to measure the biomechanical properties of the artery tissue to monitor the atherosclerosis to reduce the rupture proneness of an artery and to correlate with clinical symptoms and inflammation markers. This combined multimodal vascular imaging system 10 permits cross-sectional visualization of vasculature with high spatial resolution, broad imaging depth, and high molecular sensitivity, which is not possible by any of these technologies alone. The integrated OCT/US/PR-ARF-OCE provides the physician with a powerful tool for imaging, diagnosing, and managing vulnerable plaques.

While ultrasound-based ARF elastography has been demonstrated for many applications, it has relatively poor spatial resolution. The proposed PR-ARF-OCE uses the phase-resolved optical method to measure displacement. The phase-resolved method enables sensitive measurement of nanometer displacement. This is especially important for intravascular imaging, as better sensitivity in displacement measurement means minimal acoustic radiation forces are need be applied to a vessel wall to quantify tissue mechanical properties. Although phase-resolved dynamic OCE had been investigated previously for elastography based on shear wave propagation, the limited speed and resolution of the shear wave method made it difficult to be implemented for in vivo intravascular imaging.

In addition, frequency dependence of the ARF-OCE signal is used to quantify and characterize tissue mechanical properties. The resonant frequency of the sample is directly related to its stiffness, a stiffer material has a higher resonant frequency compared with a softer material when they are similar in mass. Fibrous, calcified and lipid plaque components have different mechanical properties. In order to differentiate the different components of plaques, we use a chirped ultrasound signal to generate a frequency sweep ARF, and measure the frequency responses of different tissues with both spectral and spatial resolution. This allows mapping of biomechanical properties of a human coronary artery with atherosclerotic plaques. By performing an analysis in the spectral domain, we automatically identify the types of plaques, such as lipid inclusion, fibrous plaque and calcified plaque based on their frequency responses.

Integration of two imaging modalities for intravascular application is known, such as combinations of IVUS with NIRS, Raman, and fluorescence imaging, including integration of OCT with fluorescence. The limitation of NIRS, Raman and fluorescence imaging is that these modes lack the capability of tomographic imaging. Intravascular applications of IVUS/PAT (photoacoustic tomography) lacks the required high resolution to quantify the thickness of the fibrous cap. Integrated OCT/US systems for intravascular imaging lack the capability to resolve tissue composition in plaque lesions. The integrated OCT/US/PR-ARF-OCE system 10 combines the advantages of near-field high resolution from OCT, far-field tissue penetration from US, and biomechanical contrast from PR-ARF-OCE. This combination enables imaging and quantification of both structure and mechanical properties of vascular lesions, information that is critical for robust diagnosis, mechanistic understanding, and treatment of vascular diseases.

The integrated OCT/US/PR-ARF-OCE system 10 has:
1. higher speed and higher resolution using phase-resolved OCT method
2. the potential for point-by-point mapping of local strains by applying localized acoustic radiation force 3. less expense by combining OCT, US, PR-ARF-OCE together through the same disposable guide wire and catheter
4. more efficient in imaging and diagnosing vulnerable plaques and monitoring therapeutic efficacy at an earlier stage by adding biomechanical property contrast to traditional IVUS OCT imaging.

Figure 1B:
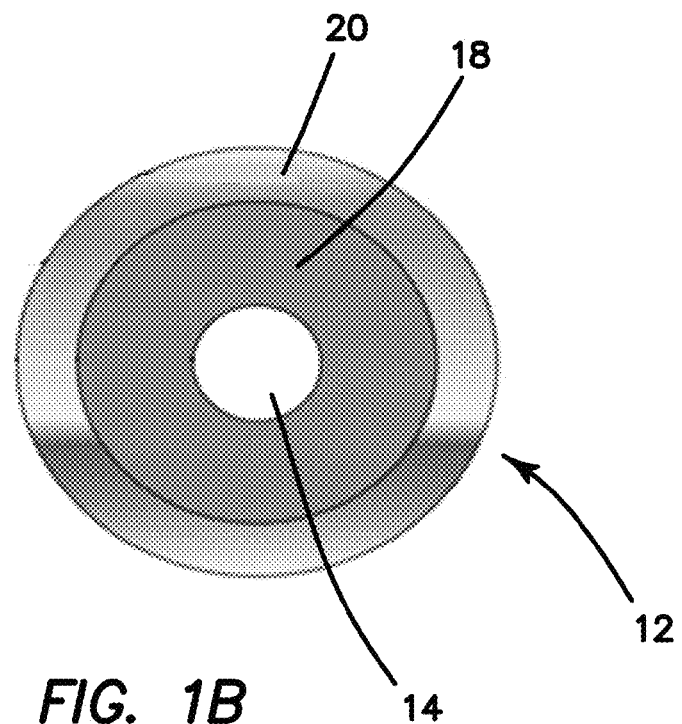

As part of the integrated system 10 we have developed an ultrasound (US) transducer 12 using single crystal composites diagrammatically shown in FIGS. 1a and 1b. A focused ring-shaped US transducer 12 with a small center hole 14 is fabricated using a lead magnesium niobate-lead titanate (PMN-PT) single crystal composite 16 usable in the frequency range of 30-50 MHz. The composite material 16 significantly improves device performance by increasing the effective electromechanical coupling coefficient ($k_{33(eff)}$) up to 0.9, which is the highest piezoelectric coupling coefficient, as well as reducing the effective dielectric constant and acoustic impedance. An increase in $k_{eff}$ result in greater transducer sensitivity and bandwidth for single crystal transducers. Decreases in the dielectric constant and acoustic impedance also increase transducer sensitivity by improving impedance match to the electric and acoustic loads on the transducer 12, which are the most desirable for building miniature IVUS transducers. The inner hole diameter is around 0.4 mm, which is large enough for mounting a fiber (not shown). The outer diameter of the ring transducer 12 is around 1.0 mm. An acoustic matching layer 18 is provided distally to composite 16 and a backing layer 22 proximately thereto. Backing layer is electrically connected to a cable 24. The optical fiber is collinearly fixed in the central hole 14 of the transducer 12. Confocal US and optical beams are launched coaxially from the monolithic device 12 included in a housing 20 toward a common reflector (not shown in FIG. 1), which changes the beams into radial scanning beams. It is to be understood that other types of US transducer materials can also be used.

The OCT, US, ARF-OCE components are integrated into a single probe 10. The schematic of the integrated probe 10 that combines a US transducer 12 of FIGS. 1a and 1b and an OCT optical fiber 36 included within a torque coil 26 is shown in FIG. 2, which illustrates the distal end of an endovascular catheter. The PMN-PT composite focused ring-shaped transducer 12 has an effective aperture of less than 1.0 mm outer diameter, with a 0.4 mm or smaller diameter opening 14 at the center to make room for the optical probe. Fiber 12 is coupled to a distal GRIN lens 32 to focus the optical beam. The coaxial ultrasound and light beams 30 have a common focal length of 4 mm, and both are steered into tissue by a 45-degree mirror 28 in their pathway. A glass mirror 28 with proper coating is fixed close to the distal or anterior surface of the hybrid OCT-US probe 12, 32, 28, 36, collectively denoted by reference numeral 38, to ensure both beams 30 are focused at the tissue target. The mirror 28 and hybrid probe 38 are properly aligned and packaged in a brass tube housing 34 in which a window is made to allow ultrasound and light beams to exit. The probe 38 is then connected to a rotary joint device 40 shown in FIG. 3 to facilitate probe rotational scanning inside a body lumen.

As shown in FIG. 3 joint 40 shows a double clad (DCF) fiber 36 optically coupled to a DCF rotary joint 50. The extending portion of hybrid probe 38 comprises a protecting jacket 44, which is rotated by electrical motor 46 coupled to jacket 44 by means of a gear train 48. US cable 24 is coupled to electrical slip ring 42, which is then coupled in turn to US cable 24 extending to the distal end of probe 38. Torque coil 26 is coupled to jacket 44 and rotated therewith. Fiber 36 extends from DCF rotary joint 50 to the distal end portion of probe 38.

Figure 4:
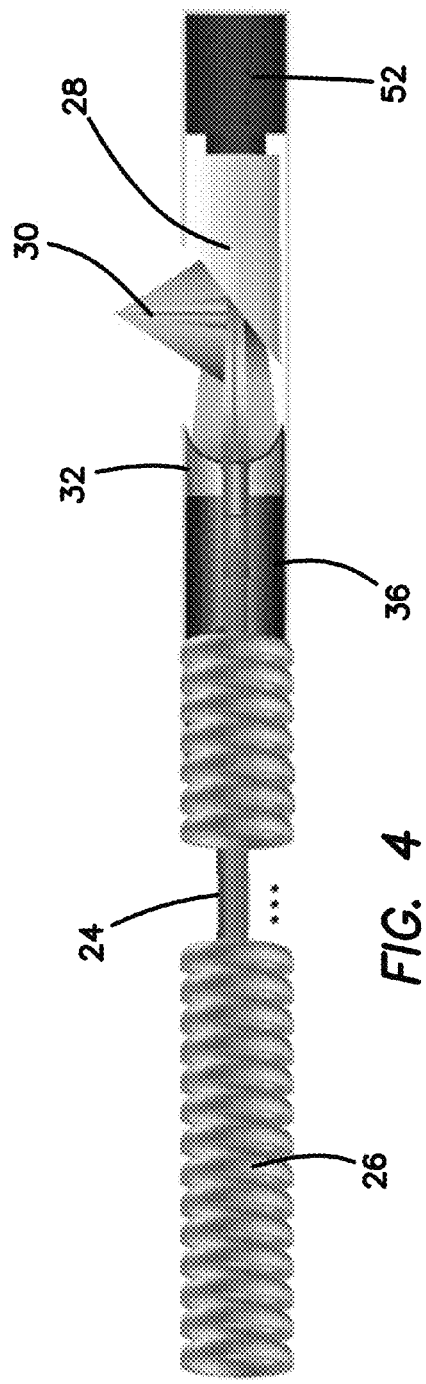
FIG. 4 is a longitudinal cutaway diagram of another embodiment of the probe of the invention wherein a distal MEMS motor is used to rotate the intraluminal probe.

An alternative method of rotating probe 38 and US and light beams 30 is to use a MEMS motor 52, which can be mounted at the distal tip of the integrated probe 38 shown in FIG. 4. We have used a MEMS motor 52 with diameter of 1.5 mm for endoscopic OCT. However, a MEMS motor 52 as small as 0.9 mm diameter is readily available. The MEMS motor 52 drives the glass mirror 28 to rotate at a speed of 30-100 revolutions per second to scan the US and light beams 30. The unique feature of this mirror-rotating design allows a more steady rotation and higher frame rate than the traditional probe-rotating method of FIG. 3.

Figure 5:
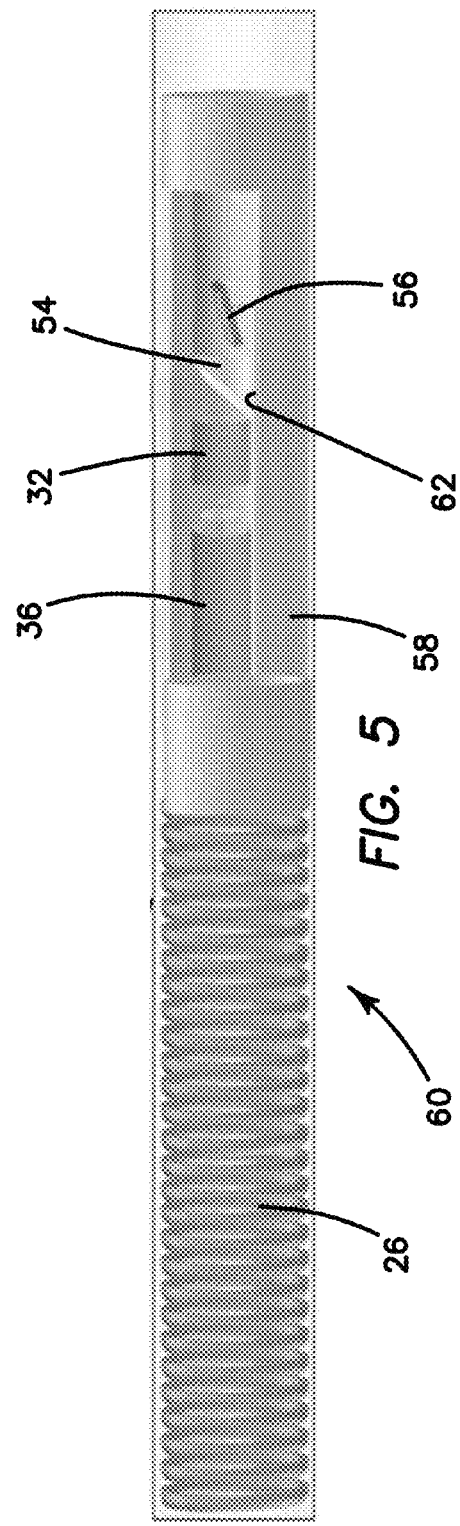
FIG. 5 is a longitudinal cutaway diagram of yet another embodiment of the probe of the invention where the ultrasound transducer is distally located in the intraluminal probe.

A coaxial design using a ring transducer allows automatically co-registration of OCT, US sensors. An alternative approach is to make a single element transducer and integrate OCT and US in a serial fashion as shown in FIG. 5. The ultrasonic transducer 56 with an aperture size of 0.4 mm×0.4 mm is built using a PMN-PT single crystal composite, which has superior piezoelectric properties for building high sensitivity US transducers in small size. The transducer 56 is fixed at the distal end of a thin-wall polyimide tube 58 with outer diameter of 0.7 mm. The OCT fiber 36 is also fixed in the same tube 58. Prism 54 provides for optical reflection of the OCT beam from the left of FIG. 5. A window 62 is made on the tube 58 to let both the light and US beams 30 exit. Transducer 56 is oriented to direct its US beam out of the window 62. The transducer wire 24 and optical fiber 36 are sealed in a torque coil 26, which is used as the drive cable. The outer diameter of the fully integrated probe 60 is less than 1.0 mm. The transducer 56 is tilted in tube 58 so that the optical beam and ultrasound beam have an overlapped target region in the tissue sample. The US transducer 56 is either flat or is shaped to provide a focused US transducer.

Another alternative approach is to have the ultrasound transducer 56 and prism 54 side by side as illustrated in FIG. 6 with all other elements the same as in the embodiment of FIG. 5.

The schematic diagram of the combined OCT/US/PR-ARF-OCE system 10 is shown in FIG. 7. The illustrated Fourier domain (FD) OCT is comprised of a fiber optic interferometer 64 with swept light source 66. An acousto-optic modulator (AOM) 68 is inserted in the reference arm 70 of interferometer 64 to provide a frequency shift that enables doubling of the imaging range. Reference arm 70 also includes conventional collimating lenses 88 and reference mirror 86. In the detection arm 72 including conventional circulators 1 and 2, 90, and 2×2 optical coupler 92, the fringe signal collected by the photodetector 74 is digitized by a high-speed digitizer (ND converter) 76, and a graphic processing unit (GPU) 78 is used for image processing and display. US imaging is acquired by a US pulser/receiver 80. ARF is generated by amplification by US power amplifier 84 of an amplitude modulated radio frequency (RF) signal from the functional generator 82 to drive the US transducer 16, 56, and phase resolved OCT will be used to detect the ARF induced displacement to quantify biomechanical properties.

The targeted fiber based OCT/US/PR-ARF-OCE imaging system 10 of the illustrated embodiment has the performance parameters summarized in Table 1:

TABLE 1

| Probe diameters | Probe scanning speed | OCT light swept speed | OCT axial resolution | OCT imaging diameter | OCE phase sensitivity to tissue displacement | US transducer | Image processing and display |
|---|---|---|---|---|---|---|---|
| <1 mm | >50-100 rotations/s | >50-200 kHz | <10-15 um | Up to 50 mm | <1 nm | >10-50 MHz | >50 Frame/s |

It is to be understood that the performance parameters are set forth as an example only and should not be understood as limiting the scope of the invention to those values shown unless set forth specifically in the claims below.

The algorithm for image reconstruction of OCT/US imaging is conventional and well know, therefore turn and consider image reconstruction of PR-ARF-OCE. ARF-OCE uses pulsed acoustic radiation force as an excitation along a tissue axial direction and detects the displacement of the tissue using OCT. Displacement is measured using imaging correlation, which has relatively low resolution, or using the phase-resolved method, which has a much better spatial resolution. For intravascular imaging, we wish to minimize the acoustic radiation force on the plaques; therefore, phase resolved ARF-OCE is implemented. The phase-resolved method has previously been used in the art to measure shear wave velocity and shear modulus. However, no research has been done on the Young's modulus along the axial direction.

For PR-ARF-OCE, we apply a square wave modulated RF signal of 10 MHz with amplitude modulation frequency of 1 kHz to the US transducer 16, 56. The ARF transmitted from the ultrasonic transducer 16, 56 compresses the tissue and triggers vibration in the longitudinal direction. This vibration is then captured by the OCT system using the phase resolved method. The instantaneous axial velocity can be extracted as, $$v(x,z,t) = \Delta\phi(x,z,t)\lambda_0/4\pi n\tau \quad \text{(Eq. 1)}$$

where and represent the lateral and axial location; denotes the phase shift between two adjacent A-lines; is the center wavelength of the light source; is the tissue refractive index; and $\tau$ is the time interval between adjacent A-lines. Within a time window of $\Delta t$, Within a time window of $\Delta t$, the displacement d can be calculated by:

$$d = \int_{t_1}^{t_2} \frac{\Delta\phi(x,z,t)\lambda_0}{4\pi n\tau} dt \quad \text{(Eq. 2)}$$

In mechanics, strain refers to the deformation of materials relative to their original length. However, this defines a single measurement of the bulk strain present in a sample with uniform strain. In OCE and ultrasound elastography, Strain is the spatial derivative of displacement along the axis of the light/ultrasound beam $$\varepsilon = \frac{\Delta d}{\Delta z} \quad \text{(Eq. 3)}$$

where $\Delta d$ is the change in displacement measured over an axial depth range $\Delta z$, which defines the axial resolution of the local strain measurement.

Young's modulus E, which provides the elasticity information of materials, is defined by:

$$E = \sigma/\varepsilon = \frac{F/A}{\varepsilon} \quad \text{(Eq. 4)}$$

where is the axial (or normal) stress acting on the sample, is the acoustic radiation force, and is the sample surface area. Both and can be measured or calibrated. Even in the case where the absolute value of F/A is not available, an image that provides variation of the Young's modulus will be of great value for diagnosis of vulnerable plaques. Since the Poisson's ratios of biological tissues generally range from 0.49 to 0.499, biological tissues are commonly assumed to be incompressible, which leads to a simple relationship between Young's modulus and shear modulus:

$$G = \frac{E}{2(1+v)} = \frac{E}{3} \quad \text{(Eq. 5)}$$

Therefore, by measuring the phase shift between sequential A-scans in response to ARF, we can characterize tissue mechanical properties such as Young's modulus and shear modulus. Assuming S(z) is the complex depth-encoded OCT fringe signal, phase change between sequential scans can be calculated by cross-correlation method:

$$\Delta\phi = \tan^{-1}\left(\frac{\text{Im}\left[\sum_{k=(n-1)M}^{nM}\sum_{j=1}^{N} s_j(z_k)s_{j+1}^*(z_k)\right]}{\text{Re}\left[\sum_{k=(n-1)M}^{nM}\sum_{j=1}^{N} s_j(z_k)s_{j+1}^*(z_k)\right]}\right) \quad \text{(Eq. 6)}$$

where N is the number of A-lines that are averaged, and M is the number of depth points that are averaged. In addition, other methods to calculate phase change can also be used.

Figure 8:
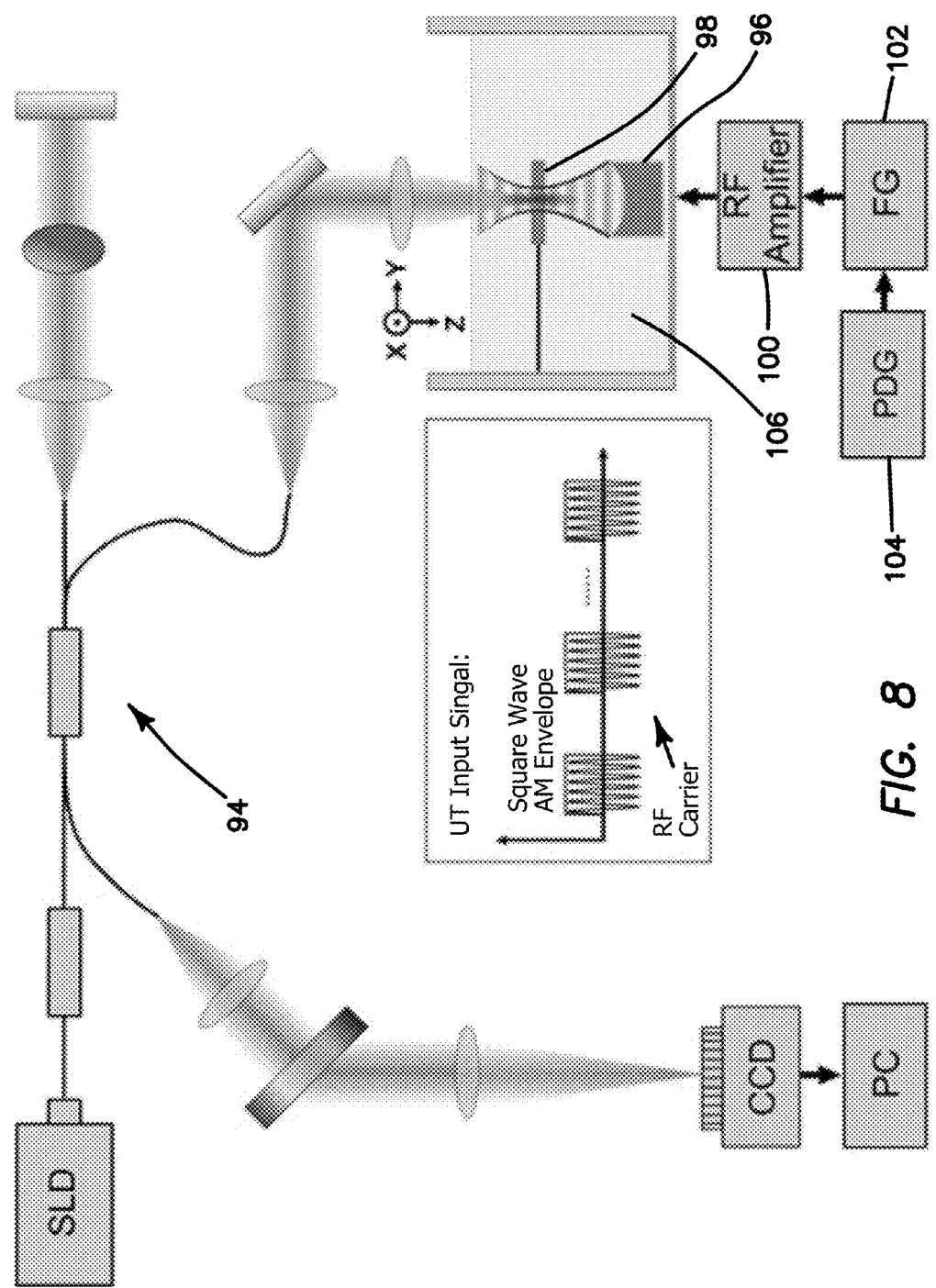
FIG. 8 is a schematic diagram of another embodiment of the integrated intraluminal imaging system of the invention.

While the relative value of strain and Young's module can be imaged with ARF-OCE, the absolute determination of these biomechanical properties requires knowledge of ARF applied to the tissue. Although ARF can be determined by simulation and calibration, adoption for in vivo quantification with constant change in geometry will be a significant challenge. A resonant phase-resolved ARF-OCE (R-PR-ARF-OCE) technique utilizing mechanical resonant frequency can be used to image and quantify tissue mechanical parameters without knowledge of ARF parameters. Using the ARF as excitation allows us to sweep different ARF frequencies and measure the frequency dependent displacement in order to determine tissue resonance frequency, which can be used to image and quantify tissue mechanical properties. In the illustrated embodiment the resonant ARF-OCE imaging was performed using an 890 nm spectral-domain OCT system shown in FIG. 8. The acoustic radiation force was generated by a focused ultrasound transducer 96, which generated a 4 MHz ultrasound wave with a lateral focal width of 2.3 mm and a length of 18 mm at around a 60 mm working distance. A RF power amplifier 100, with a linear gain of 46 dB between 0.15 MHz and 230 MHz, amplified the signals driving the transducer 96. To create a cyclic acoustic radiation force, the ultrasound transducer 96 was driven by a signal that was AM by a square wave. A function generator 102 and a pulse delay generator 104 were used to create the AM waveform, which, after power amplification, drove the ultrasound transducer 96. The pulse delay generator 104 generated a low kHz square wave (50% duty cycle AM) which modulated the amplitude of the 4 MHz burst generated by the function generator 102.

Different AM modulation frequencies were chosen to match with the resonances of phantoms and biological samples 98. The modulation frequency and amplitude were chosen for each sample in such a way that the absolute value of the phase difference induced between adjacent A-lines was large enough to enhance the sensitivity, but less than $|\pi|$ to avoid phase wrapping. For all the experiment imaging, the samples were positioned in such plane that a relatively large area of uniform ARF induced displacement was obtained. Experiment from homogeneous phantom confirmed that the ARF induced displacement is uniform over a 3.5×3.5 mm area, as shown in FIG. 16. OCT system 94, although shown component-by-component in FIG. 8, was conventional and is not further described.

The local vibration phase of the sample was detected by a phase-resolved OCT system 94, which is capable of imaging at 20 kHz with a 3.5 µm axial resolution. The phase sensitivity was measured to be 1.5 mrad, thus, yielding nanometer sensitivity in terms of displacement. Biological solid soft tissues, behaving intermediately between liquid and solid-elastic materials, are considered as viscoelastic materials, which usually can be described by the Voigt model. This model is composed of a combination of a linear spring with an elastic constant k and a dashpot with a coefficient of viscosity c. Under external force stimulation, this model can be described by $$m\ddot{z}(t)+\gamma\dot{z}(t)+kz(t)=F(t),$$

where m is the mass of the sample, z(t) is the local displacement of the sample, and F(t) is the acoustic radiation force exerted on the sample. When the deformation is small (<0.1%), the elastic constants of soft tissues can be assumed to be linear. Given the displacement of the sample, one can determine c and k and thus solves the Young's modulus under Hook's law E $$E=kL/A=(\omega^2+\lambda^2)mL/S,$$

where L and A are the thickness and area of the sample, respectively. The damping coefficient k is defined as $$\lambda=-\gamma/2m.$$

Figure 14:
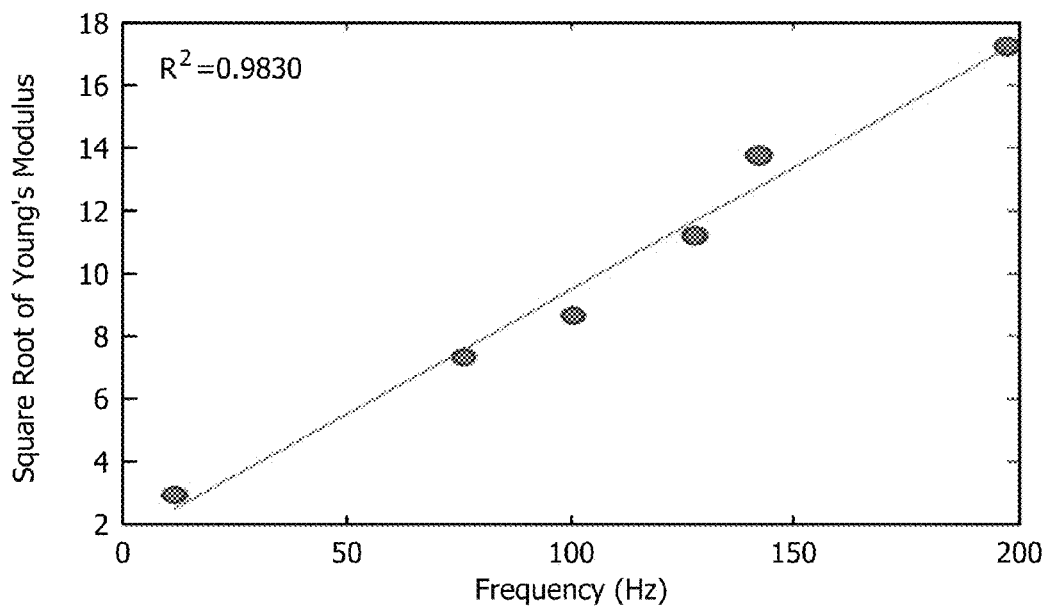
FIG. 14 is a graph showing the linear dependency of the square root of Young's modulus as a function of resonant frequency.

For a defined material, the damping coefficient is constant. Therefore, there exists a linear relationship between the square root of the modulus and the resonant frequency of the sample with a fixed geometry. To test this linear relationship, several homogeneous cylindrical phantoms with a diameter of 35 mm and a height of 3 mm were made with different ratios of silicone to the corresponding activator for different Young's moduli. The frequency responses of silicone phantoms with varying Young's moduli were measured using our resonant ARFOCE method by applying step frequency excitations. FIG. 14 shows the linear dependency of Young's modulus of the material on the square of resonant frequency with an $R^2$ coefficient closes to 1, confirming the linear relationship and showing the potential for utilizing resonant frequency to differentiate materials with varying stiffness.

Figure 9A:
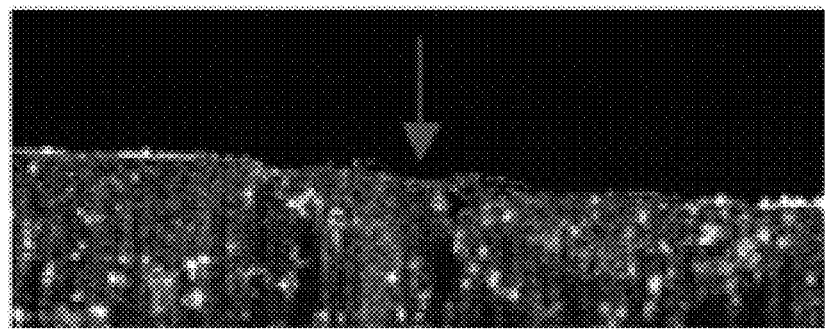
FIG. 9a is an OCT intensity image of side-by-side agarose phantom.
Figure 9B:
FIG. 9b is an OCE image under 4 MHz with 500 Hz AM modulation ARF excitation.
Figure 9C:
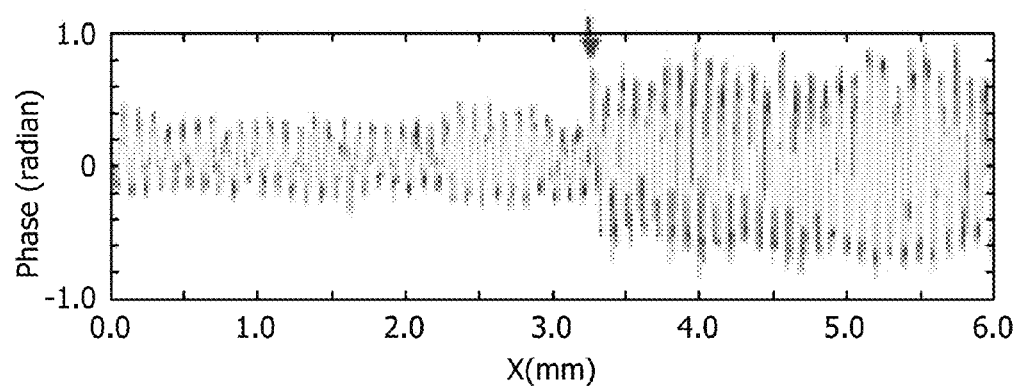
FIG. 9c is a graph of phase amplitude averaged over the depth of tissue. The red arrow indicates the boundary between two sides of 7% and 3.5% agarose film. The total length is 6 mm.
Figure 10:
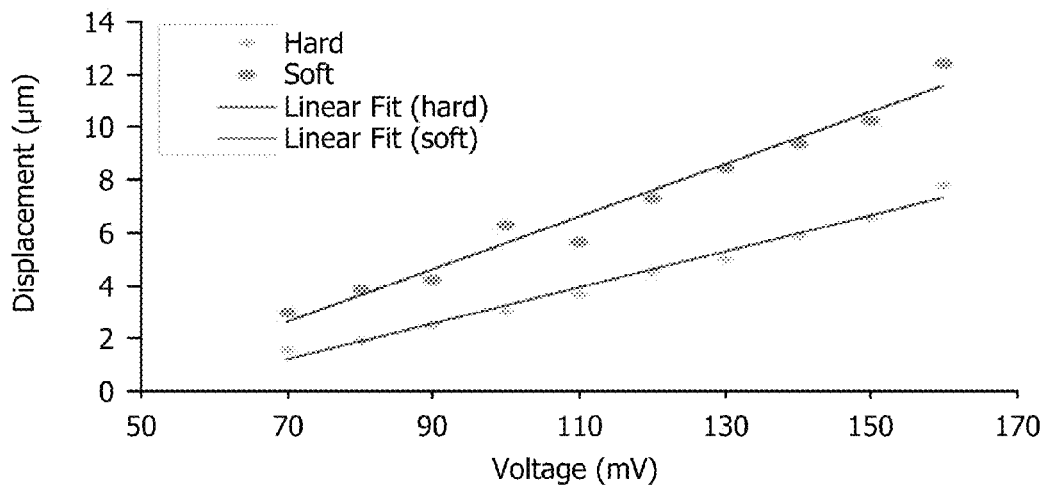
FIG. 10 is a graph of the axial displacement of a phantom to acoustic radiation force (ARF) verses a pre-amplified voltage supplied to the transducer.
Figures 11A, 11B, 11C:
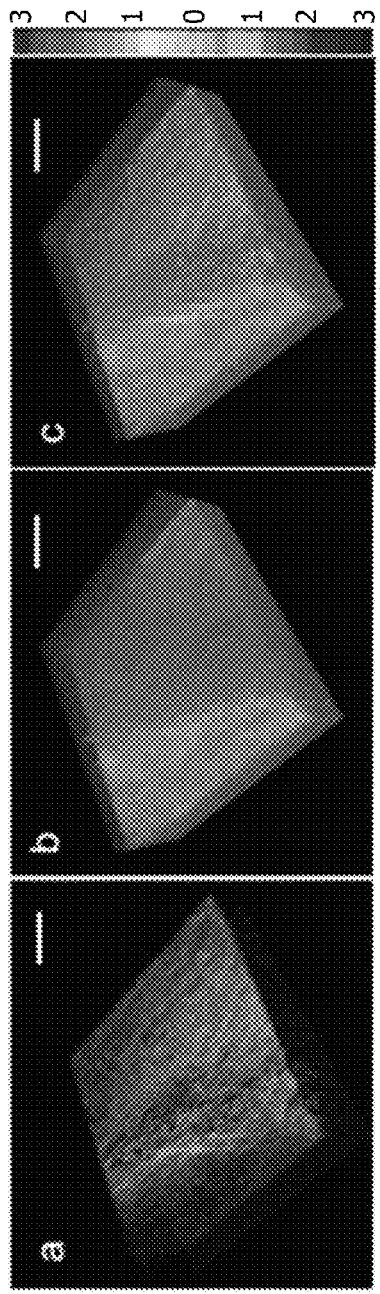
FIG. 11a is a three dimensional OCT imaging of an agarose tissue mimicking phantom.
FIG. 11b is a PR-ARF-OCE image of the phantom.
FIG. 11c is the fused OCT and PR-ARF-OCE image. The phantom is excited with a 500 Hz square wave modulated ARF. The depicted scale bar is 1 mm.

Results from a tissue phantom consisting of a thin film made of agarose with two different concentrations side by side are shown in FIGS. 9a and 9b in an OCT image and in FIG. 9c in a graph. The concentration of agarose is 7% and 3.5% for each side, respectively. The OCT image of the phantom is shown in FIG. 9a, from which the two sides of agarose film with different concentrations cannot be clearly distinguished. The phase change map of the OCE image for the agarose film under ARF from an ultrasound transducer 96, driven at RF frequency of 4 MHz and AM modulation of 500 Hz, is shown in FIG. 9b. The phase change amplitude averaged over depth is shown in FIG. 9c. The boundary (arrow) between two sides of the phantom with different concentrations can be clearly visualized in FIGS. 9b and 9c There are two ways to form the OCE image in the illustrated embodiments. The first way uses the measurement of ARF induced displacements when amplitude modulated ARF with fixed a frequency, which gives the relative Young's module and other mechanical properties. This first way is useful when only the relative values of tissue mechanical properties for imaging contrast is needed. The second way is to measure the frequency dependence of the ARF induced displacement when chirped amplitude modulated ARF is applied to tissue. A linear relationship between voltage applied to the ARF transducer 96 and the phase shift measured is observed in FIG. 10. Since the ARF acting on both sides of the phantom was the same, the ratio of Young's modulus between two sides can be quantified from the ratio of the measured phase shifts. The ratio of Young's modulus between the 7% and 3.5% agarose material within the two sides of the phantom measured by phase shifts is 1:3.06, which is consistent with the value measured using a standard compression test (1:3.17). We also performed three dimensional imaging of this phantom as shown in FIGS. 11a and 11b. The OCT image in FIG. 11a shows no differentiation between two sides of phantom with different stiffness. However, the three dimensional PR-ARF-OCE image (FIG. 11b) clearly delineated the two materials with different stiffness. These preliminary results clearly indicate that PR-ARF-OCE image can be used to quantify mechanical properties of a tissue.

Figures 12A, 12B, 12C:
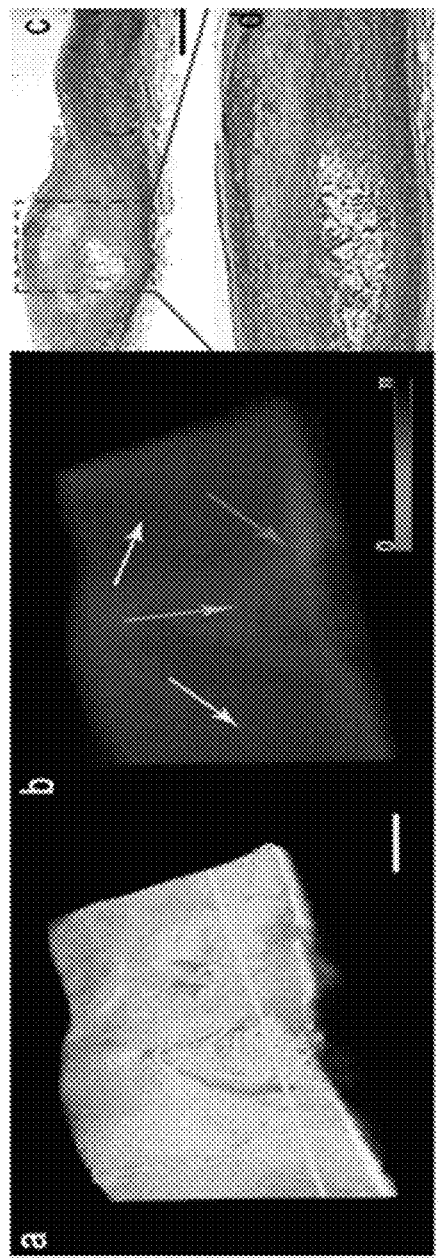
FIGS. 12a, 12b are PR-ARF-OCE images of human coronary artery.
FIG. 12c is a histological close-up image of an atherosclerotic lesion corresponding to across blue line location in FIG. 12a and of the dotted portion of FIG. 12c. The scale bars are 1 mm.

To demonstrate the potential of this technology in imaging plaque, we have performed imaging of a section of atherosclerotic human coronary artery with PA-ARF-OCE as shown in FIGS. 12a, 12b and 12c. An OCT intensity image, shown in FIG. 12a, provides a general morphological view of the tissue with no obvious evidence of the presence of atherosclerosis. By applying a 500 Hz chirped acoustic radiation force onto the tissue, a strong vibration phase contrast can be clearly imaged using ARF-OCE in FIG. 12b. The region indicated by the yellow arrows in ARF-OCE image is characterized by less vibration and therefore represents less elastic, stiffer tissue such as plaques. The strong vibration representing softer tissue is indicated by blue arrows. The stiffer tissue, in this case atherosclerotic plaque, is clearly distinguished from the softer (usually normal) tissue area highlighted by brighter colors. This result clearly shows that PR-ARF-OCE can delineate diseased tissue from normal tissue and has the potential to quantitatively characterize tissue mechanical properties. The algorithm takes into account of the frequency response of the ARF-OCE signal, which may provide calibration free mechanical properties of tissues.

Although relative value of strain and Young's module can be imaged with ARF-OCE, the absolute determination of these biomedical properties requires knowledge of ARF applied to the tissue. Although ARF can be determined by simulation and calibration, a method that is independent of ARF will be much better. We will also use the mechanical resonant frequency to effectively distinguish tissues of varying stiffness. Under small deformation, there is a direct relation between Young's module and resonant frequency:

$$E=4\pi^2 f^2 l^2 \rho$$

where f is the resonance frequency, l is the thickness of the sample, and r is the density. Therefore, measurement of frequency dependence of ARF-OCE signal will allow us to determine the biomechanical properties directly.

Figure 13A:
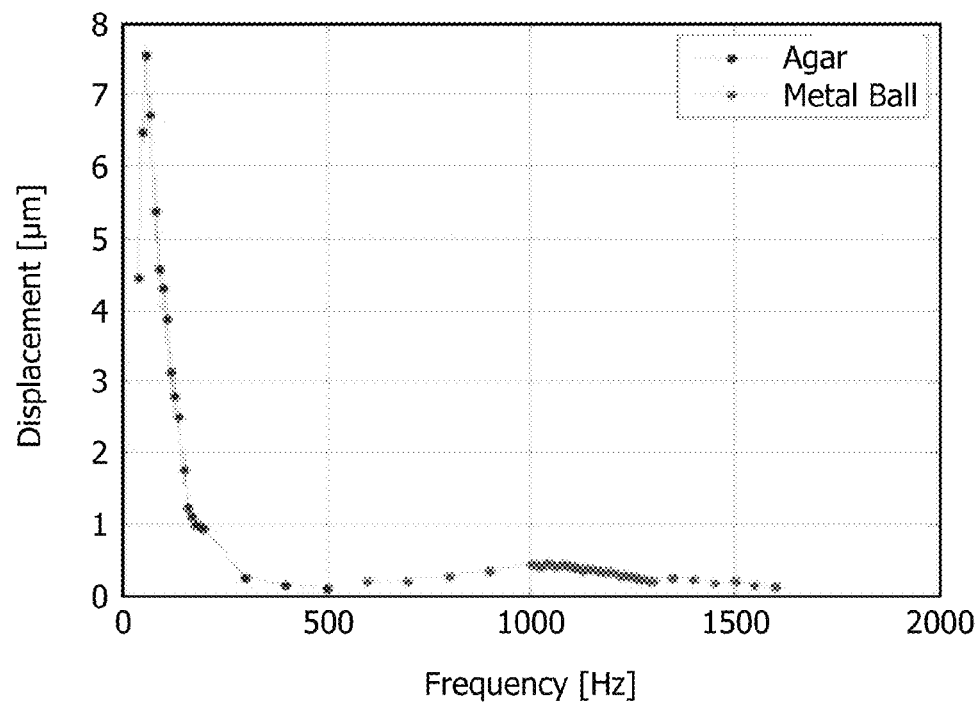
FIG. 13a is a graph of the frequency response spectrogram of agar and a metal ball. The resonant frequency of agar and metal ball are 60 Hz and 1080 Hz, respectively.
Figure 13B:
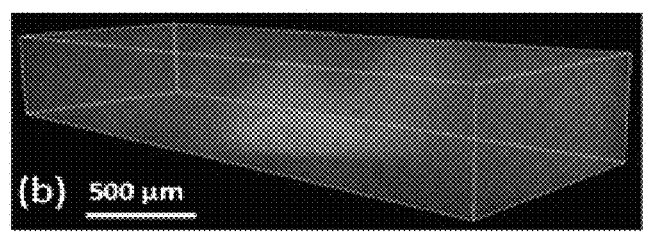
FIG. 13b is a three dimensional ARF-OCE image excited at modulation frequency of 1080 Hz.
Figure 13C:
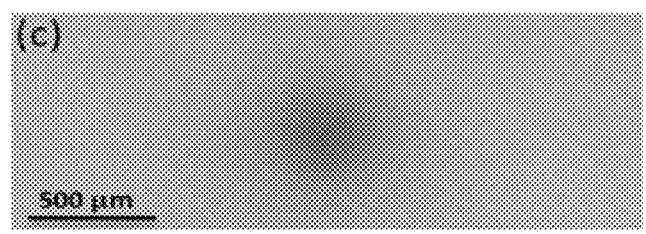
FIG. 13c is a sample picture.

To demonstrate the mechanical contrast of the resonant ARF-OCE method, we first tested an agar phantom (0.8% agar, mass concentration and 0.4% intralipid, volumetric concentration) with a 513 μm metal ball embedded inside. For all experiments, the acoustic wave was applied perpendicular to the surface of the metal ball from the bottom of the water tank while the optical beam was applied perpendicularly from the top. The measured frequency response spectrogram of agar and metal ball was plotted in FIG. 13a. With different vibrational amplitudes due to significant elastic property differences, very strong resonances at 60 Hz and 1080 Hz were observed for the agar and stainless steel ball, respectively. This indicated that if a driving frequency of 1080 Hz were to be applied to the sample, one should be able to differentiate the stainless steel ball from the surrounding agar. We imaged the agar phantom under a modulation frequency of 1080 Hz, which was the resonant frequency of the stainless steel ball. As expected, the metal ball produced a distinctive vibration amplitude in comparison with the surrounding agar, yielding high-contrast in the resonant elastography map in FIG. 13b. Only the top of the metal ball can be seen in the images due to the highly reflective nature of the metal ball. The measured resonant frequency of the metal ball is not only related to the material but also affected by the size and shape of the metal ball. We then tested the resonant ARF-OCE method on an agar phantom with a piece of silicone embedded inside. Silicone is stiffer than the surrounded agar but has similar optical properties as the agar. We imaged the agar phantom under a modulation frequency of 1250 Hz, which is around the resonant frequency of the embedded silicone. As expected, the silicone piece is barely discernible in the OCT image as shown in FIG. 15a. However, the silicone piece produced a distinctive vibration amplitude in comparison with the surrounding agar, yielding high-contrast in the resonant elastography map as shown in FIG. 15b. The fused OCT and OCE image is shown in FIG. 15c. These results again demonstrate that our resonant ARF-OCE can provide a strong mechanical contrast based on the resonant frequency of the material.

Finally, to test the feasibility of applying this resonant ARF-OCE technique to image and differentiate atherosclerotic plaques, ex vivo resonant ARF-OCE imaging of a section of post-mortem human coronary artery with atherosclerotic plaques was performed at varying frequencies. The human coronary artery was cut open, flattened, and preserved in saline solution prior to the experiment to keep it well hydrated. During the experiment, the human coronary was immersed in phosphate-buffered saline (PBS) solution, which served as both the coupling media for the ultrasonic wave and also the bio-environment for the tissue, and laterally scanned 3.5 mm where the vibration of the sample induced by the acoustic radiation force was evenly distributed. After ARF-OCE imaging, the sample was fixed using 10% formalin solution and sectioned for histological analysis. The histological sections were interpreted by a pathologist who had no access to the information provided by the resonant ARF-OCE method. The processed sample histology shown in FIGS. 17d and 17e was confirmed as a necrotic core fibroatheroma (NCFA) with a fibrous cap, pointed by black arrows, on top of a necrotic lipid core (NC). Regions I and II of the fibrous cap are thin loose fibrous tissues about 100 μm thickness, where the plaque is more likely to rupture. In region III, the fibrous tissue becomes thicker and denser, which is considered as the stable area of the plaque. Tiny microscopic nodules of calcium salts were found at the boundary between the lipid core and the fibrous cap. The structure of the NCFA was reconstructed in the OCT image in FIG. 17a, due to the limited penetration depth; only the fibrous cap and part of the lipid core can be seen in the OCT image. The structure revealed in the OCT image corresponded very well with the histological sections in FIG. 17d. The resonant ARF-OCE distinguished different components in the plaque at varying frequencies. The thin, loose fibrous cap (regions I and II) showed higher resonant amplitude at a 500 Hz driving frequency in FIG. 17b, as opposed to the thick, dense fibrous cap (region III) which showed very weak vibration at this frequency. Conversely, when the sample was excited under 800 Hz, the thick, dense fibrous cap portion started to show a stronger motion than the portion with the thin, loose fibrous cap. In FIG. 17c the left part of the thin fibrous cap shows higher vibration than the one on the right side of the image. This may be a result of the calcium salts deposit on the left of the plaque, where higher reflection for the acoustic radiation force induced a relative stronger vibration than in the area without microscopic calcium nodules. Since the mechanical characteristics of the fibrous cap determines the stability of the plaque, the resonant-ARF-OCE method could provide useful mechanical information about the fibrous cap and thus may serve as a predictor of atherosclerotic plaque stability and provide useful information during clinical interventions, such as stent and balloon catheter insertion.

In summary, we have presented a spectral and resonant ARF-OCE technique, which takes advantage of the fact that materials respond primarily at their mechanical resonant frequencies, to effectively distinguish samples with varying stiffness. This method provides an additional type of contrast to previously reported acoustic radiation force optical coherence elastography technique. Resonant frequencies of silicone phantoms with different Young's modulus were investigated first with a focused ultrasound transducer that generated local acoustic radiation force stimulation at step-driven frequencies on the phantoms. A well fitted linear dependency curve of the resonant frequency on the square root of Young's modulus is presented and thus validated the hypothesis of the method. The feasibility of this method on differentiating materials with different stiffness was tested on an agar phantom with a hard inclusion. Both the frequency response spectrum and the imaging results demonstrate the effectiveness of delineating the isolated hard inclusion by means of stimulating the sample at the resonant frequency. Driven by the ultimate goal of applying the proposed resonant ARF-OCE technique to medical diagnosis and prognosis, we furthermore performed the resonant ARF-OCE measurement on a section of post-mortem human coronary artery with calcifications. A two dimensional OCT-structural image and a relative ODT phase map correlated with the histological image. The phase map highlighted regions with calcifications featuring a dominant vibration in comparison with the normal tissue surrounding. The results of the current study demonstrate the capability of the resonant ARF-OCE method as a non-invasive assessment of pathological tissue with the potential for use in clinical settings in the future.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An integrated intraluminal imaging system for diagnosis and management of a disease exhibiting changes in biomechanical properties of tissues comprising:
    an intraluminal probe;
    an optical coherence tomography (OCT) interferometer including an optical fiber disposed in the intraluminal probe, the optical fiber for delivering an optical beam and receiving a returned optical signal through the intraluminal probe from the tissues;
    an ultrasound (US) subsystem having an ultrasound transducer disposed in the intraluminal probe, the ultrasound transducer having a ring-shape and delivering an ultrasound beam and receiving a returned ultrasound signal through the intraluminal probe from the tissues, the optical fiber collinearly fixed in a central hole of the ultrasound transducer such that the optical beam and the ultrasound beam are coaxially and confocally launched towards a common reflector;
    an acoustic generator coupled to the ultrasound transducer for delivering an acoustic radiation force (ARF) to the tissues, the optical coherence tomography interferometer receiving a returned ARF optical signal due to displacement of the tissues in response to the acoustic radiation force from which returned ARF optical signal a phase resolved acoustic radiation force optical coherence elastography (PR-ARF-OCE) image can be formed; and
    a computer coupled to optical coherence tomography interferometer, to the ultrasound transducer, and to the acoustic generator for controlling the same and for processing the returned optical signal simultaneously with each of the returned ultrasound signal and the returned AU optical signal to generate corresponding datasets from each to form an image derived from combining datasets of the returned optical signal, the returned ultrasound signal and the returned ARF optical signal,
    wherein the processing simultaneously differentiates tissues with different biomechanical properties and measures structural and mechanical properties of the differentiated tissues.

2. A method of diagnosis and management of a disease exhibiting changes in biomechanical properties of tissues, the method comprising:
    providing an integrated intraluminal imaging system comprising:
        a. an intraluminal probe;
        b. an optical coherence tomography interferometer including an optical fiber disposed in the intraluminal probe;
        c. an ultrasound subsystem having a ring-shaped ultrasound transducer disposed in the intraluminal probe; and
        d. an acoustic generator generating an acoustic radiation force (ARF) signal coupled to the ultrasound transducer;
    delivering an optical beam through the intraluminal probe to the tissues;
    receiving a returned optical signal through the intraluminal probe from the tissues for communication thereof to the optical coherence tomography interferometer;
    delivering an ultrasound imaging beam from the ultrasound transducer, wherein the ultrasound imaging beam is confocal and coaxial with the optical beam;

receiving a returned ultrasound imaging signal through the intraluminal probe from the tissues in an ultrasound receiver;

delivering a resonant phase resolved acoustic radiation force (ARF) to the tissues from the ultrasound transducer through the intraluminal probe;

receiving a returned ARF optical signal in the optical coherence tomography interferometer measuring displacement of the tissues in response to the acoustic radiation force; and processing the returned optical signal simultaneously with each of the returned ultrasound imaging signal and the returned ARF optical signal to generate corresponding datasets from each in a computer to form an image derived from combining datasets of the returned optical signal, the returned ultrasound signal and the returned ARF optical signal, wherein the processing simultaneously differentiates tissues with different biomechanical properties and measures structural and mechanical properties of the differentiated tissues.

* * * * *